United States Patent [19]
Brezoczky

[11] Patent Number: 5,781,649
[45] Date of Patent: Jul. 14, 1998

[54] SURFACE INSPECTION OF A DISK BY DIFFRACTION PATTERN SAMPLING

[75] Inventor: Blasius Brezoczky, San Jose, Calif.

[73] Assignee: Phase Metrics, Inc.

[21] Appl. No.: 632,246

[22] Filed: Apr. 15, 1996

[51] Int. Cl.⁶ .................................................. G06T 7/00
[52] U.S. Cl. ............................ 382/108; 382/141; 356/371
[58] Field of Search ............................ 382/108, 141, 382/312, 321; 73/104, 105; 356/237, 446, 371; 369/109; 250/559.45; 348/128

[56] References Cited

U.S. PATENT DOCUMENTS

| | | | |
|---|---|---|---|
| 3,964,830 | 6/1976 | Ikeda et al. | 356/237 |
| 4,334,780 | 6/1982 | Pernick | 356/237 |
| 4,363,118 | 12/1982 | Roach et al. | 369/58 |
| 4,541,716 | 9/1985 | Crooks et al. | 356/237 |
| 4,674,875 | 6/1987 | Koizumi | 356/237 |
| 5,173,605 | 12/1992 | Hayes et al. | 250/306 |
| 5,187,367 | 2/1993 | Miyazaki et al. | 250/306 |
| 5,193,385 | 3/1993 | Nishioka et al. | 73/105 |
| 5,307,336 | 4/1994 | Lee et al. | 369/112 |
| 5,392,079 | 2/1995 | Fedorov et al. | 351/212 |
| 5,428,442 | 6/1995 | Liu et al. | 356/237 |
| 5,436,448 | 7/1995 | Hosaka et al. | 250/306 |

*Primary Examiner*—Jon Chang
*Attorney, Agent, or Firm*—Blakely Sokoloff Taylor & Zafman

[57] ABSTRACT

An optical inspection apparatus detects anomalies by reflecting a beam of coherent light off the surface of a sample. An anomaly present on the surface causes the reflected beam to be diffracted at an angle which corresponds to a scale of the anomaly. An optical detection array is positioned to receive the reflected diffraction pattern and produce an electrical signal which corresponds to the diffraction angle of the reflected pattern. The electrical signal may then be processed to determine the location and scale of the anomaly from the detected diffraction angle.

10 Claims, 2 Drawing Sheets

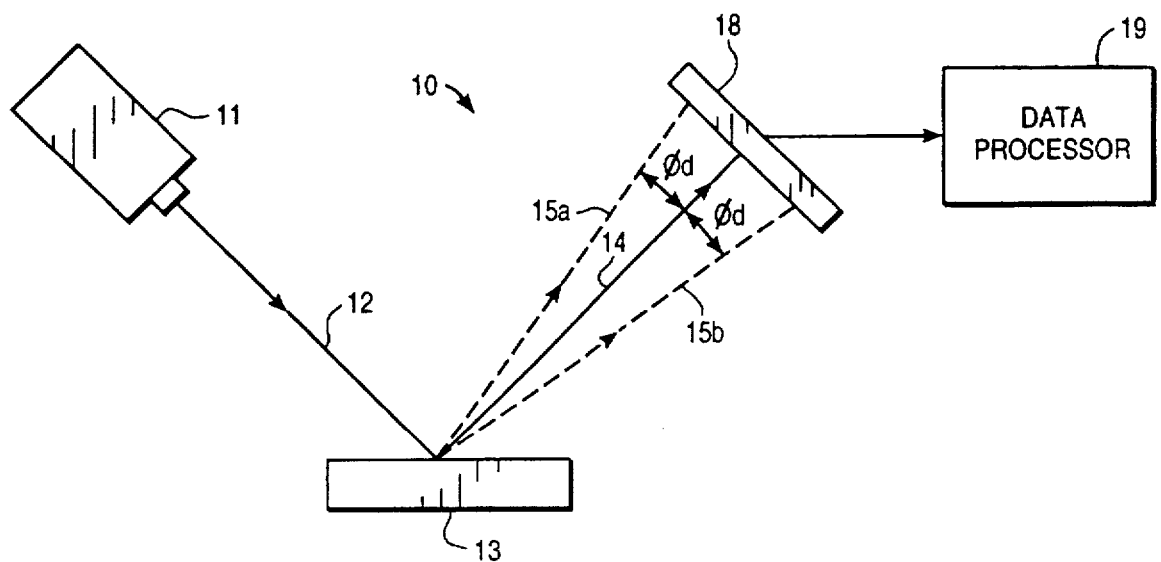
FIG_1
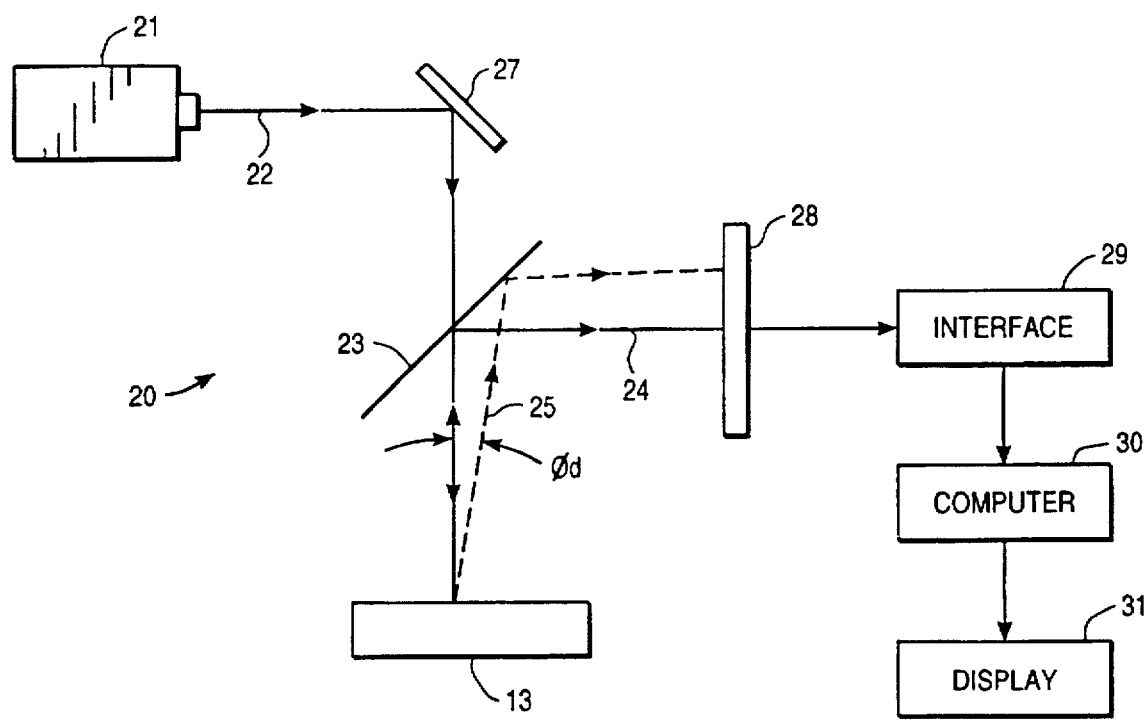
FIG_2

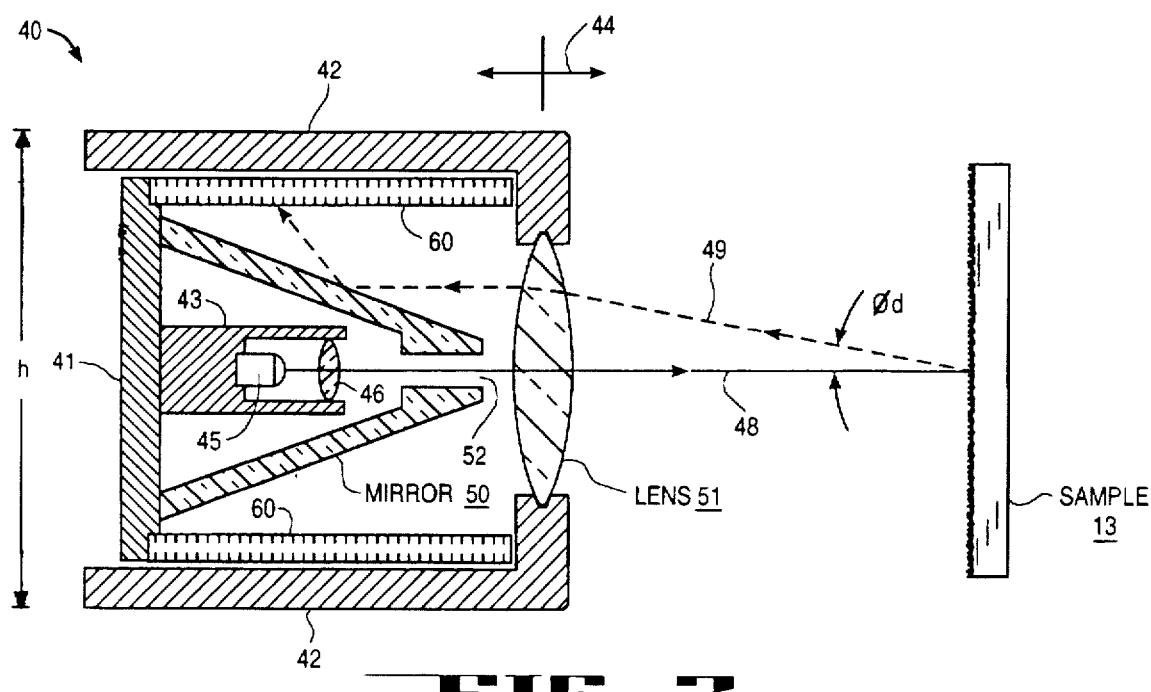
FIG_3
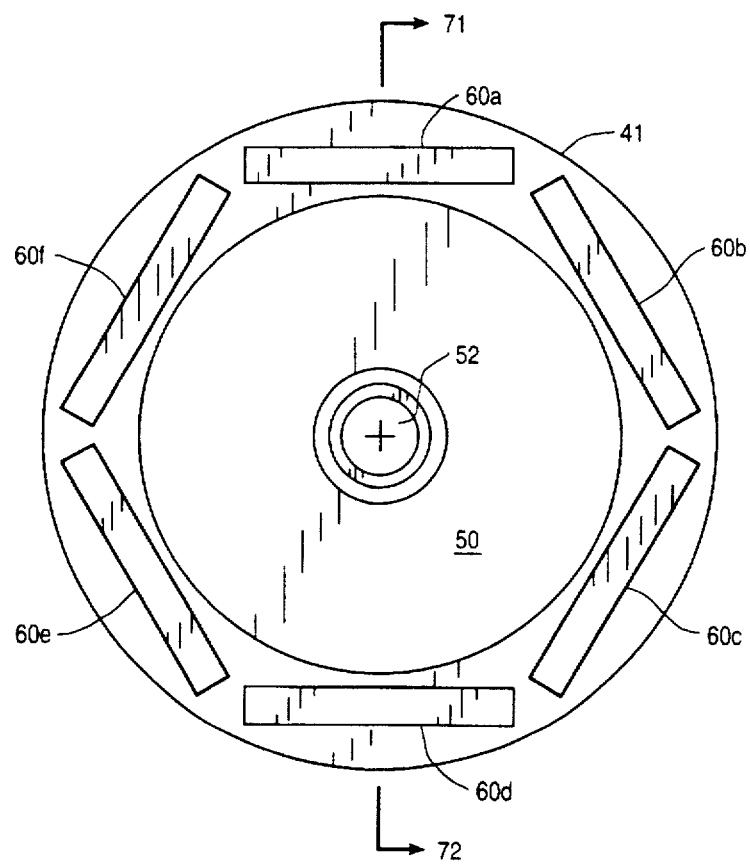
FIG_4

SURFACE INSPECTION OF A DISK BY DIFFRACTION PATTERN SAMPLING

FIELD OF THE INVENTION

The present invention relates to the field of optical pattern recognition. More specifically, the invention relates to the field of apparatus and methods for inspecting the surface of a flat sample for microscopic flaws.

BACKGROUND OF THE INVENTION

Numerous industries have a need for an apparatus capable of inspecting the surface of a machined and highly-polished article of manufacture. For example, the disk drive recording industry relies upon the manufacture of extremely smooth aluminum or nickel substrates upon which have been deposited a magnetic layer of material. In order to certify the usefulness of the magnetic disk, the surface is normally inspected for defects, flaws, contaminate particles, etc., all of which can generally be categorized as surface anomalies. Very often it is desired to provide a mapping of the number, locations, and size of the anomalies so that writing of magnetic information can be avoided in these areas. In situations where the anomalies are very numerous or are particularly large in size, the entire disk may be rejected.

One of the difficulties associated with past techniques for inspecting disk samples have been the texture roughness associated with the disk surface. During the inspection process, the texture roughness should be suppressed since the anomalies are typically qualified based upon a minimum diameter and depth relative to the mean roughness of the disk surface. Developing methods and apparatus which suppress texture roughness has been problematic.

Another shortcoming of prior approaches has been that the inspection time is prohibitively long for a manufacturing or certification process. That is, it is desirable that the detection time be as short as possible so that a high throughput of samples can be achieved.

As will be seen, the present invention overcomes the shortcomings of the prior art by providing an apparatus for detecting anomalies on the surface of a highly-polished sample. The invented system utilizes optical pattern recognition techniques that make the high-rate automatic inspection of samples feasible.

SUMMARY OF THE INVENTION

The invention covers an optical inspection apparatus that is well-suited to automatic surface inspection of highly-polished samples having defects and flaws that are of microscopic size.

Tiny anomalies present on the surface of the sample are detected utilizing a laser that generates a beam of coherent light. The beam of laser light is directed by optics onto the surface of the sample. An anomaly present on the surface causes the laser beam to be diffracted as it is reflected from the surface. The reflected light is diffracted at an angle which corresponds to a scale of the anomaly. An optical detection array is positioned to receive the reflected diffraction pattern. The detection array is organized to produce an electrical signal which corresponds to the diffraction angle of the reflected pattern. The electrical signal may then be processed to determine the location and scale of the anomaly from the detected diffraction angle.

BRIEF DESCRIPTION OF THE DRAWINGS

The present invention will be understood more fully from the detailed description which follows and from the accompanying drawings, which, however, should not be taken to limit the invention to the specific embodiments shown, but rather are provided for explanation and understanding only.

FIG. 1 is a diagram illustrating one embodiment of the surface inspection apparatus of the present invention.

FIG. 2 illustrates another embodiment of the present invention.

FIG. 3 is a cross-sectional side view of another embodiment of the surface inspection apparatus of the present invention.

FIG. 4 is a frontal, plane view of the embodiment shown in FIG. 3.

DETAILED DESCRIPTION

A surface inspection apparatus capable of high-rate automatic operation is described. In the following description, numerous specific details are set forth such as particular elements, power levels, spacings, etc. in order to provide a thorough understanding of the present invention. However, it will be obvious to one skilled in the art that the invention may be practiced without these specific details. In other instances, well known techniques, materials, components, etc. have not been shown or described in detail in order to avoid unnecessarily obscuring the invention.

The invented apparatus will be described in several embodiments suitable for use in detecting anomalies present in samples having specifications such as those listed in Table I below.

TABLE I

| Dimension: | 5 1/4 inch O.D. (disk) |
|---|---|
| Periodic Roughness: | $-4 \times 10^{-6}$ inch p.p. (machining) |
| Texture Roughness: | $-1 \times 10^{-6}$ inch p.p. (polishing) |
| Anomalies: | |
| Diameter: | $20 \times 10^{-6}$ inch (minimum) |
| Depth: | $-8 \times 10^{-6}$ inch (minimum) |
| | from mean roughness |
| Materials: | 1. Al Alloy |
| | 2. 304/440 |
| | 4. Nickel Phosphate |
| | 5. $Al_2O_3$ on Al |
| | 6. Carbon |

With reference to FIG. 1, there is shown a surface inspection apparatus 10 according to the present invention. Apparatus 10 comprises a laser source 11 which includes a laser and associated optics for producing a beam of coherent light 12 having a characteristic wavelength. For instance, an ordinary helium-neon laser may be utilized wherein the wavelength of light beam 12 is equal to 0.6328 microns.

Light beam 12 is directed onto the surface of sample 13. The light reflected from the sample is then detected on a properly positioned photodetection array 18. Photodetection array 18 is configured to transform the light energy of the reflected beam into an electrical signal that may be provided to a data processor 19. Data processor 19 may comprise an ordinary microprocessor of a typical computer system.

The present invention employs diffraction pattern sampling of laser beam 12 to determine the scale of an anomaly present on the surface of sample 13. If no anomaly were present on the surface of sample 13, the reflected beam 14 would come to a near point focus at the detector position. Tiny flaws on the surface of sample 13, however, cause differential phase shifts in the reflection. These differential phase shifts cause the light to be diffracted as it is reflected off the surface of sample 13. The diffraction pattern produced by an anomaly is shown in FIG. 1 by dashed lines 15a and 15b in the reflected beam. This diffraction can be analyzed rigorously using well-known mathematical formulations. The salient point, however, is that tiny, microscopic surface flaws cause large angles of diffraction.

The apparatus of the present invention utilizes the diffraction pattern produced by the anomaly to determine the scale of the defect. For instance, fine scale details or anomalies may lead to diffraction angles (labeled $\phi_d$ in FIG. 1) ranging from zero to 45 degrees. The finer the scale of the defect or flaw, the larger the diffraction angle produced. By way of example, a defect may cause diffraction scattering on the order of $\phi_d$ given by the equation:

$$\sin \phi_d = \lambda/d$$

where $\lambda$ represents the wavelength of the laser light and d is the scale of the anomaly. In a typical implementation, a helium-neon laser may be utilized ($\lambda=0.6328$ microns) to detect an anomaly having a size d=100 microinches, thereby resulting in a diffraction angle of approximately 14.4 degrees. To repeat, the angle is determined according to the present invention by the electrical response produced by photodetection array 18. This electrical response may then be processed utilizing data processor 19 to determine characteristic information concerning the anomaly.

With reference now to FIG. 2 there is shown another embodiment of the apparatus of the present invention. Apparatus 20 of FIG. 2 comprises laser 21 (and associated optics) which produces a laser beam 22 that is directed onto the surface of sample 13 utilizing an ordinary mirror 27 and 50% waveplate 23. As can be seen, the beam is directed through waveplate 23 such that the reflection from the sample surface is projected by wave plate 23 onto photodetection array 28.

The diffraction pattern of reflected beam 24 is shown in FIG. 2 by dashed line 25. The intensity of the diffracted pattern is recorded on array 28 for subsequent processing by digital computer 30. Interface 29 provides appropriate interfacing of the electrical signaling produced by array 28 with computer 30. The results may then be displayed by display device 31, which may include well-known devices such as a plotter, flat panel display, cathode ray tube, etc.

Practitioners in the art will appreciate that by utilizing moveable mirrors and/or moveable samples, the entire surface of the sample may be inspected with the apparatus of the present invention. The electrical signal produced in response to each location may be stored within the computer so that an entire mapping of the surface can be produced. Such a mapping would show the number, locations, and scale of the anomalies present on the surface of sample 13.

In a typical implementation, photodetection array 28 may comprise an array of commercially-available photodiodes. Alternatively, charge-coupled semiconductor devices (CCDs) may also be utilized. The important function of the photodetection array in the present invention is to provide transformation of the light intensity produced by the diffraction pattern into an electrical response which corresponds to the diffraction angle. In other words, the photodetection array is utilized to capture the angle of incidence of the diffracted, reflected light.

With reference now to FIG. 3, there is shown a cross-sectional side view of another embodiment of the present invention. Optical inspection apparatus 40 comprises a rigid base 41 attached to a mount 43. Mount 43 supports laser diode 45 and lens 46. The laser beam emitted by diode 45 is directed along a longitudinal axis which passes through a central opening 52 of a conical mirror 50. Note that the assembly which includes mount 43, laser diode 45, and lens 46 is housed within an interior cavity of conical mirror 50. Furthermore, conical mirror 50 is supported by base 41, as are the set of photodetection arrays 60 and lens mount 42. By way of example, a typical height dimension, h, for apparatus 40 may be about 150 mm.

Lens mount 42 is a moveable, rigid support for lens 51, which focuses light beam 48 onto the surface of sample 13. Lens mount 42 is moveable attached to base 41 and may be adjustably positioned in a direction indicated by arrow 44, i.e., along the longitudinal axis of light beam 48. Note that this direction is generally orthogonal to the surface of sample 13. Although a particular mechanism for movably engaging lens mount 42 with base 41 is not shown in FIG. 3, any one of a variety of well-known mechanical methods may be employed. For instance, an ordinary tooth-and-gear mechanism, or a simple incised advancing spiral thread mechanism, may be used adjust the position of lens 51 with respect to the laser light source. Of course, other implementations will be apparent to those possessing ordinary skill in the mechanical or optical arts.

Base 41 also supports a set of photodetection arrays 60, which are best seen in the frontal plane view of FIG. 4. It should be understood that base 41, lens mount 42 and mount 43 may comprise a wide variety of materials which provide rigid support. For example, aluminum, stainless steel, plastics, etc., may all by utilized in the construction of inspection apparatus 40.

The operating principals of apparatus 40 are identical to those discussed in conjunction with previous embodiments. That is, light beam 48 generated by laser 45 is projected through opening 52 of conical mirror 50 and is focused by lens 51 onto a determined location of sample 13. An anomaly present at the determined location produces a diffraction pattern in the reflected light. The diffraction pattern is produced with a characteristic diffraction angle $\phi_d$, which is shown in FIG. 3 by dashed line 49. Lens 51 then directs the reflected light pattern onto conical mirror 50. Mirror 50, in turn, reflects the diffracted light onto a lineal position of photodetection array 60.

It is appreciated that the diffraction pattern is substantially circular in shape; hence, the reason for a set of circumferentially arranged photodetection arrays 60 about conical mirror 50. This aspect of the invention is best illustrated in FIG. 4 where detection arrays 60a–60f are shown disposed in a circle about mirror 50. As explained above, detection arrays are attached to base 41. (Note that the view of FIG. 3 is taken along sectional cut lines 71–72.)

Depending upon the scale of the anomaly that exists on the surface of sample 13, the diffraction angle of the reflected pattern will vary. As a result, the lineal position at which the reflected pattern is received on arrays 60 will vary in accordance with the diffraction angle. That is, a small diffraction angle causes the reflected light (from the surface of sample 13, through lens 51, and off of mirror 50) to have a maximum intensity at an array 60 location which is far from base 41. On the other hand, a very large diffraction angle will produce a maximum intensity in the reflected pattern at an array location near to base 41.

The electrical response produced by the photodetection elements of arrays 60 indicates the position at which the reflected beam intensity is greatest. In this way, the diffraction angle is correlated to the electrical response produced by arrays 60 so that the scale of the anomaly can be determined. As before, the individual photodetection elements may comprise photodiodes or charge-coupled devices. Furthermore, the number of photodetection elements arranged about conical mirror 50 may vary according to the level of electrical response it is desired to produce.

I claim:

1. An apparatus for inspecting the surface of a sample for an anomaly comprising:

a base;

a conical mirror attached to the base, the conical mirror having a central opening to a cavity;

a laser providing a light beam with a characteristic wavelength, the laser beam being mounted to the base with the cavity such that the light beam emerges through the central opening along a longitudinal axis;

a lens;

a lens mount movably attached to the base to position the lens along the longitudinal axis, the light beam emerging through the central opening and passing through the lens, the lens forming the light beam into a convergent beam directed upon the surface of the sample; and an array of photodetection elements arranged circumferentially around the conical mirror, the photodetection elements extending in a direction substantially parallel to the longitudinal axis, wherein a reflection of the convergent beam is diffracted as it is reflected from the surface of the sample with a diffraction pattern that corresponds to a scale of the anomaly, the diffraction pattern producing an electrical response from the array of photodetection elements indicative of a characteristic of the diffraction pattern.

2. The apparatus of claim 1 wherein the reflection from the surface passes through the lens and is reflected off the conical mirror onto a lineal position of the array of photodetection elements.

3. The apparatus of claim 2 wherein the array of photodetection elements comprises a plurality of photodiode arrays arranged circumferentially around the conical mirror, each photodiode array including a matrix of photodiodes.

4. The apparatus of claim 2 wherein the array of photodetection elements comprises a plurality of charge-coupled device arrays arranged circumferentially around the conical mirror, each charge-coupled device array including a matrix of charge-coupled devices.

5. The apparatus of either claim 3 or 4 wherein the laser comprises a laser diode.

6. The apparatus of claim 5 wherein the lens mount is movably attached to the base utilizing a tooth-and-gear mechanism.

7. The apparatus of claim 5 wherein the sample comprises a magnetic recording disk.

8. The apparatus of claim 5 wherein a diffraction angle, $\phi$, associated with the diffraction pattern is given by the equation:

$$\sin \phi = \lambda d$$

where $\lambda$ is equal to the characteristic wavelength of the light beam, and d is approximately equal to the scale of the anomaly.

9. The apparatus of claim 5 further comprising:

a processor means coupled to the array of photodetection elements for processing the electrical signal.

10. The apparatus of claim 9 further comprising:

a display means for producing a visual display of a location and the scale of the anomaly on the surface of the sample.

* * * * *